US 8,965,484 B2

(12) United States Patent
Quelever et al.

(10) Patent No.: US 8,965,484 B2
(45) Date of Patent: Feb. 24, 2015

(54) METHOD AND APPARATUS FOR GENERATING A PERFUSION IMAGE

(75) Inventors: Ronan Quelever, Versailles (FR); Laurent Launay, St Remy les Chevreuse (FR); Amy Deubig, Dousman, WI (US)

(73) Assignee: General Electric Company, Schenectady, NY (US)

( * ) Notice: Subject to any disclaimer, the term of this patent is extended or adjusted under 35 U.S.C. 154(b) by 638 days.

(21) Appl. No.: 13/095,515

(22) Filed: Apr. 27, 2011

(65) Prior Publication Data

US 2012/0275674 A1 Nov. 1, 2012

(51) Int. Cl.
*A61B 5/05* (2006.01)
*A61B 6/00* (2006.01)
*A61B 6/03* (2006.01)
*G06T 7/00* (2006.01)

(52) U.S. Cl.
CPC .............. *A61B 6/503* (2013.01); *A61B 6/032* (2013.01); *A61B 6/481* (2013.01); *A61B 6/504* (2013.01); *A61B 6/5217* (2013.01); *A61B 6/5223* (2013.01); *G06T 7/0083* (2013.01); *G06T 7/0081* (2013.01); *A61B 6/507* (2013.01); *G06T 2207/10081* (2013.01); *G06T 2207/30048* (2013.01); *G06T 2207/30101* (2013.01)
USPC ........................................................ 600/425

(58) Field of Classification Search
USPC .......... 600/407, 425–427, 436; 382/131, 133
See application file for complete search history.

(56) References Cited

U.S. PATENT DOCUMENTS

| 6,112,112 | A | * | 8/2000 | Gilhuijs et al. | 600/425 |
|---|---|---|---|---|---|
| 6,549,606 | B1 | | 4/2003 | Vaillant et al. | |
| 6,888,916 | B2 | | 5/2005 | Launay et al. | |
| 6,980,682 | B1 | | 12/2005 | Avinash et al. | |
| 7,565,000 | B2 | | 7/2009 | Capolunghi et al. | |
| 2004/0153128 | A1 | * | 8/2004 | Suresh et al. | 607/14 |
| 2004/0225328 | A1 | * | 11/2004 | Okerlund et al. | 607/9 |
| 2005/0041769 | A1 | * | 2/2005 | Launay et al. | 378/4 |
| 2005/0254708 | A1 | * | 11/2005 | Jolly et al. | 382/173 |
| 2007/0244389 | A1 | | 10/2007 | Hoppel et al. | |
| 2007/0287906 | A1 | * | 12/2007 | Kadir et al. | 600/411 |
| 2007/0299351 | A1 | * | 12/2007 | Harlev et al. | 600/509 |
| 2008/0188734 | A1 | | 8/2008 | Suryanarayanan et al. | |
| 2009/0022375 | A1 | | 1/2009 | Fidrich et al. | |
| 2011/0150309 | A1 | * | 6/2011 | Barfett et al. | 382/131 |
| 2011/0164796 | A1 | * | 7/2011 | Hundley et al. | 382/128 |
| 2013/0077838 | A1 | * | 3/2013 | Lamash et al. | 382/128 |

FOREIGN PATENT DOCUMENTS

WO    WO2010/023618    *  3/2010

* cited by examiner

*Primary Examiner* — Christopher Cook
(74) *Attorney, Agent, or Firm* — Dean D. Small; The Small Patent Law Group

(57) ABSTRACT

A method of displaying image data for a tissue of an organ includes acquiring a three-dimensional (3D) projection dataset using a Computed Tomography (CT) imaging system, performing a segmentation of the 3D projection dataset that includes a plurality of voxels, performing a perfusion viability cluster analysis to identify myocardium voxels, grouping the myocardium voxels into viable clusters and non-viable clusters based on a density and a location of the myocardium voxels, and generating an image of the myocardium and a coronary tree using the viable clusters and the non-viable clusters. An imaging system and a non-transitory computer readable medium are also described herein.

18 Claims, 7 Drawing Sheets

METHOD AND APPARATUS FOR GENERATING A PERFUSION IMAGE

BACKGROUND OF THE INVENTION

The subject matter disclosed herein relates generally to medical imaging systems and, more particularly, to an apparatus and method for classifying image voxels and generating a perfusion viability image using the classified voxels.

Measurements of cardiac perfusion, in particular to evaluate blood supply to the myocardium, are of importance in assessing whether patients may are experiencing low blood flow perfusion through the myocardium. Perfusion measurements are typically performed using a conventional Myocardial Perfusion Imaging (MPI) technique. The conventional MPI technique is typically implemented using, for example, a Positron Emission Tomography (PET) system or a Single Photon Emission Computed Tomography (SPECT) system. However, implementing the conventional MPI technique using the PET or the SPECT imaging system may result in increased scan times and thus an increase in radiation exposure to the subject.

Therefore, Computed Tomography (CT) imaging systems may also be utilized to measure cardiac perfusion to diagnose coronary artery disease. More specifically, CT imaging systems utilize both anatomical and functional methods to determine the perfusion and viability of the myocardium. CT imaging systems also provide functional information about flow through microvasculature within the myocardium imaging following the injection of a contrast agent. The functional information allows for the visualization of the perfusion or blood flow through regions of myocardium that may be affected.

In operation, the conventional CT imaging system utilizes various tools to generate perfusion viability maps of the myocardium. However, the conventional perfusion maps may include noise which reduces the physician's ability to measure or evaluate the perfusion in the myocardium. Additionally, the perfusion maps generated by the conventional CT imaging system are different than perfusion maps generated by the conventional PET or SPECT imaging system. More specifically, the perfusion maps generated by the conventional CT imaging system may display the myocardium using various colors or other indicia that are different than the colors and indicia that is utilized in perfusion maps generated by the conventional PET or SPECT imaging system. Thus, a physician that is familiar with the colors and indicia of a typical PET perfusion image may be less familiar with the colors and indicia used to generate a conventional CT perfusion image making it more difficult for the physician to assess cardiac perfusion and thus form a diagnosis of the patient.

BRIEF DESCRIPTION OF THE INVENTION

In one embodiment, a method of displaying image data for a tissue of an organ is provided. The method includes acquiring a three-dimensional (3D) projection dataset using a Computed Tomography (CT) imaging system, performing a segmentation of the 3D projection dataset that includes a plurality of voxels, performing a perfusion viability cluster analysis to identify myocardium voxels, grouping the myocardium voxels into viable clusters and non-viable clusters based on a density and a location of the myocardium voxels, and generating an image of the myocardium and a coronary tree using the viable clusters and the non-viable clusters.

In another embodiment, a Computed Tomography (CT) imaging system is provided. The CT imaging system includes an x-ray source, a detector configured to receive x-rays from the x-ray source, and a computer coupled to the detector. The computer is programmed to acquire a three-dimensional (3D) projection dataset using a Computed Tomography (CT) imaging system, perform a segmentation of the 3D projection dataset that includes a plurality of voxels, perform a perfusion viability cluster analysis to identify myocardium voxels, group the myocardium voxels into viable clusters and non-viable clusters based on a density and a location of the myocardium voxels, and generate an image of the myocardium and a coronary tree using the viable clusters and the non-viable clusters.

In a further embodiment, a non-transitory computer readable medium is provided. The computer readable medium is encoded with a program to instruct a computer to acquire a three-dimensional (3D) projection dataset using a Computed Tomography (CT) imaging system, perform a segmentation of the 3D projection dataset that includes a plurality of voxels, perform a perfusion viability cluster analysis to identify myocardium voxels, group the myocardium voxels into viable clusters and non-viable clusters based on a density and a location of the myocardium voxels, and generate an image of the myocardium and a coronary tree using the viable clusters and the non-viable clusters.

DETAILED DESCRIPTION OF THE INVENTION

Figure 1:
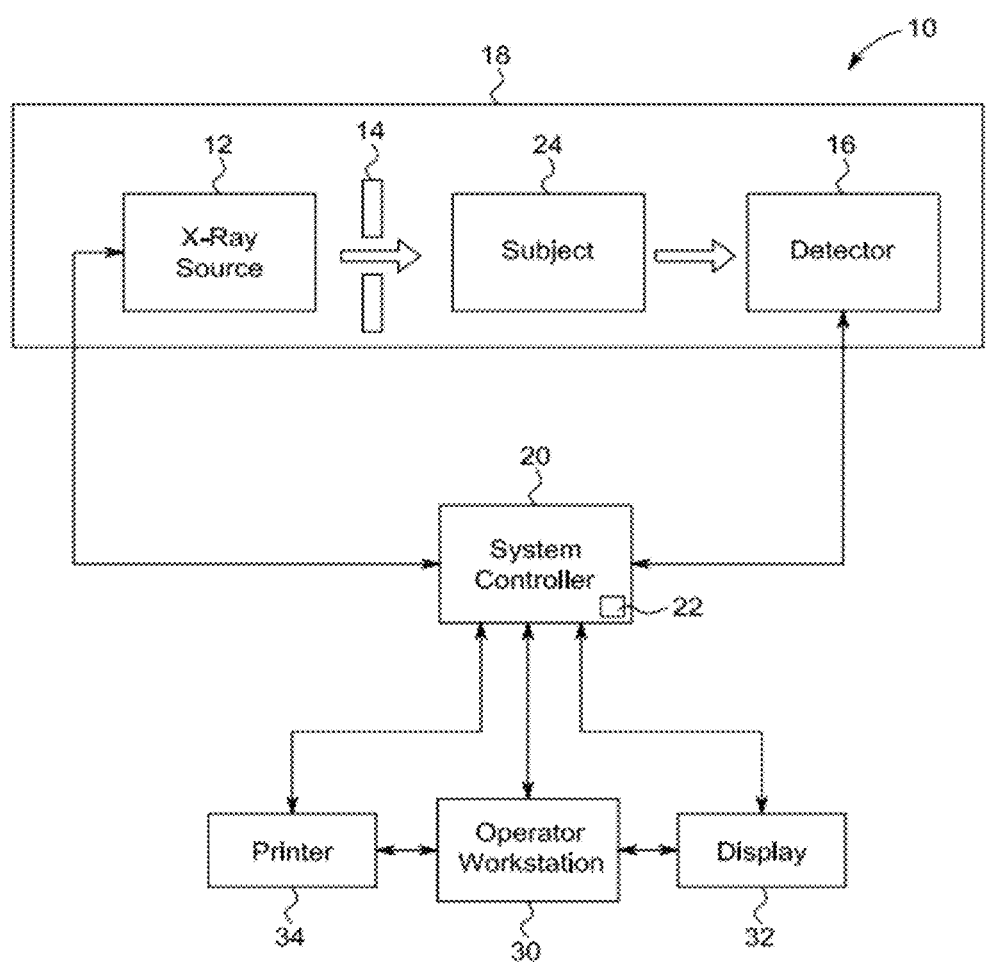
FIG. 1 is a simplified schematic block diagram of an exemplary imaging system formed in accordance with various embodiments of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or multiple pieces of hardware). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

Referring to the drawings, FIG. 1 is a simplified block diagram of an imaging system. In the exemplary embodiment, the imaging system is a Computed Tomography (CT) imaging system 10. The CT imaging system 10 includes an x-ray source 12, a collimator 14 adjacent to the x-ray source 12, and a detector 16. The x-ray source 12 and the detector 16 are mounted on a gantry 18 to enable the x-ray source 12 and the detector 16 to rotate about an examination axis.

The CT imaging system 10 further includes a system controller 20 coupled to the x-ray source 12 and the detector 16 for controlling operation of the x-ray source 12 and the detector 16. The system controller 20 may supply both power and control signals for imaging examination sequences. In general, the system controller 20 controls the operation of the CT imaging system 10 to execute examination protocols and to process acquired image data, also referred to herein as projection data. The system controller 20 may include at least one image processing module 22 that is configured to receive the projection data and to generate at least one image that may be utilized to visualize perfusion in the myocardium of a subject 24, such as a patient. The module 22 may be implemented as a processor that is programmed to carry out various functions in accordance with routines stored in an associated memory (not shown). The associated memory may also serve to store configuration parameters, operational logs, raw and/or processed projection data, and so forth.

The system controller 20 may be coupled to one or more external devices via a communications interface. Such devices may include, for example, an operator workstation 30 for interacting with the CT imaging system 10, processing or reprocessing projection data, generating and/or viewing images, and so forth. Other external devices may include a display 32 and/or a printer 34. In general, these external devices 30, 32, and/or 34 may be local to the image acquisition components, or may be located remotely from these components, such as elsewhere within a medical facility, institution or hospital. The external devices 30, 32, and/or 34 may also be located in an entirely different location, and linked to the system controller 20 via one or more configurable networks, such as the Internet, intranet, virtual private networks, and so forth. Such remote systems may be linked to the system controller 20 by any one or more network links. Additionally, although described in a medical setting, it is contemplated that the benefits of the various embodiments described herein accrue to medical imaging systems and non-medical imaging systems such as baggage scanning systems used in an airport or a rail station.

The CT imaging system 10 is configured to form images of the subject 24 utilizing attenuation information received from the detector 16. More specifically, the detector 16 converts x-ray photons received on a surface of the detector 16 to lower energy light photons. The photons are converted to electric signals, referred to herein as projection data, which are processed to reconstruct an image of internal anatomy within the subject 24.

In operation, the projection data is processed to reconstruct an image that corresponds to a two dimensional (2D) slice taken through the subject 24. One method for reconstructing an image from a set of projection data is referred to in the art as the filtered back projection technique. The reconstruction process converts the integral attenuation measurements into an image representing attenuation measurements of the subject 24. The attenuation measurements are typically converted into units of CT numbers or Hounsfield units. Thus, a CT image is made up of multiple x-ray attenuation measurements. The image is represented as a matrix of numbers, with each individual number in the image matrix representing a three-dimensional (3D) volume element in the scanned part, called a "voxel." To obtain a visual image, each voxel is represented as a 2D picture element, or "pixel." Each pixel has a shade of gray representing the x-ray attenuation within the corresponding voxel.

Figure 2:
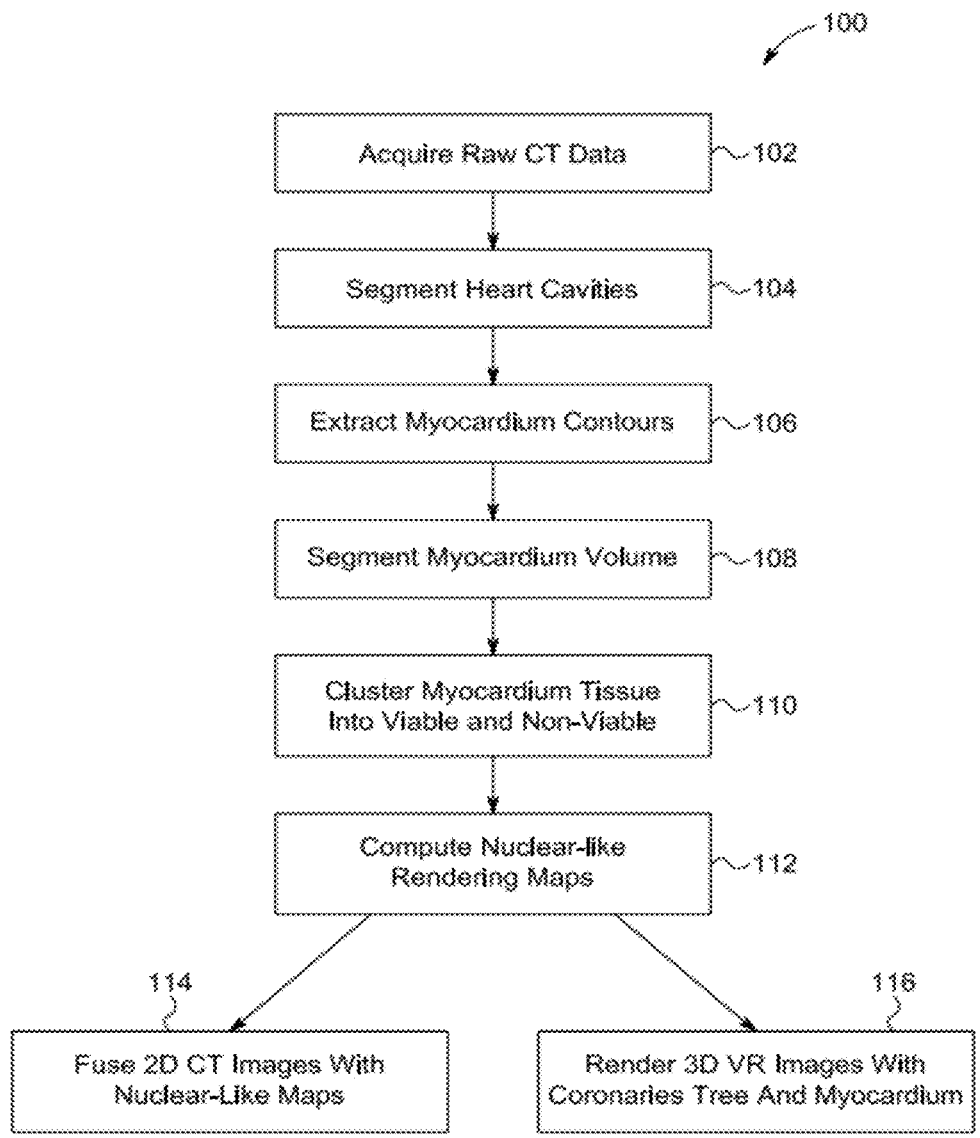
FIG. 2 is a flowchart of a method for generating a perfusion image of a subject in accordance with various embodiments.

FIG. 2 is a flowchart of an exemplary method 100 for generating a perfusion image of a subject utilizing the CT imaging system 10 shown in FIG. 1. The method 100 may be embodied as a set of instructions that are stored on the module 22, for example.

At 102, an imaging scan of the subject 24 is performed to generate a set of raw CT data, also referred to herein, as projection data or three-dimensional (3D) volumetric data. More specifically, the CT imaging system 10 performs a scan to generate the projection data. In the exemplary embodiment, the CT imaging system is configured to perform a scan of a region of interest that includes the myocardium, and the projection data is a set of three-dimensional (3D) data that is represented by three volumetric axis over a predetermined time period. The projection data is representative of attenuation measurements of the region of interest including the myocardium.

At 104, a segmentation algorithm is performed on the raw projection data to separate projection data related to the heart cavity from projection data related to other anatomical structures. In operation, the segmentation algorithm is configured to locate objects of interest, such as the heart cavity, and separate projection data of the heart cavity from projection data of objects of lesser or no interest, such as the lungs.

The segmentation algorithm uses the principle whereby it is generally assumed that bones, and other anatomical features, may be differentiated from the heart cavity by determining the density of each voxel in the projection data. The density generally represents the intensity value of the voxel. Based on the density values of each of the voxels, the heart cavity may be distinguished from the other anatomical features. Accordingly, at 104 the segmentation algorithm compares the density value for each voxel in the projection data to a predetermined density value, such as using a thresholding process. In the exemplary embodiment, the predetermined density value may be a range of predetermined density values. The predetermined density value range may be automatically set based on a priori information of the heart cavity. Optionally, the predetermined range may be manually input by the operator. In one embodiment, if the density value of a voxel is within the predetermined range, the voxel is classified as a heart cavity voxel. Otherwise, the voxel is classified as not belonging to the heart cavity. It should be realized that the segmentation algorithm may also be utilized with other segmentation techniques to identify the heart cavity. Additionally, as should be appreciated other suitable segmentation algorithms may be used.

Accordingly, at 104 the heart and/or heart cavities projection data, e.g. voxel information, that is identified using the segmentation algorithm, is utilized to generate a projection dataset that includes only voxel information representing the heart and/or heart cavities. Separating the voxel information by removing data that is not of interest (i.e., everything external to the heart, and even the aorta and heart cavities) from the original CT volume dataset, facilitates reducing the number of voxels remaining to be processed.

At 106, the segmented information of the heart cavity identified at 104 is utilized to extract contours of the myocardium. The contours are utilized to form a projection dataset that includes voxel information of the myocardium volume. In the exemplary embodiment, at least one contour that delineates the boundaries of the myocardium of the left ventricle (LV contour) are extracted. In one embodiment, the LV contour may be extracted by utilizing a manual or semi-automatic algorithm. For example, an operator may manually locate and extract the LV contour. In another embodiment, an enhancement detection algorithm may be used to differentiate regions of the LV ventricle from other regions of the heart. For example, an edge detection algorithm that analyzes the image data may be utilized to identify contours of the left ventricle, and more specifically, the inner and outer walls of the myocardium.

The myocardium volume is segmented using the contours of the myocardium generated at 106. The myocardium contours may be determined using, for example, a thresholding (contrast intensity algorithm as discussed above). More specifically, it is assumed that density of the voxels forming the myocardium is different than the density of voxels forming other regions of the heart cavity. Therefore, based on the density values of each of the voxels, the myocardium may be distinguished from the heart cavity. Accordingly, at 106 a segmentation algorithm compares the density value for each voxel in the projection data around the LV cavity to a predetermined density value. In the exemplary embodiment, the predetermined density value is a range of density values. The predetermined density range may be automatically set based on a priori information of the heart cavity and the myocardium. Optionally, the predetermined range may be manually input by the operator.

In one embodiment, if the density value of a voxel is within the predetermined range, the voxel is classified as a myocardium voxel. Otherwise, the voxel is classified as a heart cavity voxel. It should be realized that the segmentation algorithm may also be utilized with other segmentation techniques to identify the myocardium. Additionally, as should be appreciated other suitable segmentation algorithms may be used.

Therefore, the methods described herein are configured to utilize a segmentation algorithm to differentiate the heart and/or heart cavity from other anatomical features, differentiate the myocardium from other regions of the heart to identify contours of the inner and outer walls of the myocardium, and utilize a segmentation algorithm to separate the myocardium from other organs to specifically identify projection data of the LV myocardium.

At 108, the contours acquired at 106 are utilized to segment the myocardium volume. Specifically, the myocardium volume is segmented as follow by identifying voxels that are located between the inner and outer walls of the myocardium as defined by the contours described above. Accordingly, any voxels that are located between the two contours obtained at 106 are classified as a myocardium voxel.

At 110, a clustering analysis is performed on the segmented myocardium projection data generated at 108. Cluster as used herein, is defined as a group of voxels having similar characteristics, such as for example, similar densities and/or locations. In operation, the cluster analysis divides the segmented projection data of the myocardium into groups, i.e. clusters, such that similar voxels (those of similar signal intensity or location) belong to the same cluster and dissimilar voxels to different clusters. Cluster analysis is specifically performed to partition the segmented myocardium data into viable and non-viable voxels. Viable clusters typical represent healthy tissue and non-viable clusters typically represent diseased or non-health tissue. Clustering is based on the premise that voxels of the myocardium may be separated based on the signal intensity of the voxels used to form the image of the myocardium and other voxels. Damaged myocardium displays as either hypo-enhanced or hyper-enhanced compared with normal myocardium.

Therefore, at 110, the clustering analysis is performed on the segmented myocardium projection data generated at 108 to initially partition the segmented myocardium projection data into clusters of viable and non-viable voxels based on the intensity of each voxel in the projection data. For example, if the voxel intensity is within the predetermine range, the voxel is classified as a viable. If the voxel is not within the predetermined range, the voxel is classified as non-viable. Various methods may be utilized to differentiate voxel intensities. In the exemplary embodiment, the intensity of each voxel may be displayed on a color scale and/or a grey scale.

The mean intensity and standard deviation of segmented myocardium voxels are then calculated. For each voxel, either a Z-score or a T-test can be used to determine the probability that there is a difference in the intensity values between the myocardium and the tissue in question. For example, a voxel may be assigned a value indicating where the voxel falls in a Gaussian or Normal distribution.

The Z-score and/or the T-score, for each voxel, may be determined in accordance with:

$$Z = \frac{\overline{X} - \mu}{\sigma/\sqrt{N}} \text{ or } T = \frac{\overline{X_1} - \overline{X_2}}{\sigma\sqrt{\frac{1}{N_1} + \frac{1}{N_2}}} \qquad \text{Equation 1}$$

where X is the intensity value for a single voxel;
σ is the standard deviation of the voxel intensity values
μ is the mean of the voxel intensity values; and
N is the number of voxels in the myocardium.

The probabilities or the Z-score can be mapped on an image. Mapping probabilities within the range of the myocardium or other types of tissues allows for improved visualization of the area of interest. Thus, in one embodiment, the voxels are initially clustered into clusters that include viable voxels or a non-viable voxels based on the value of the Z-score and/or the T-score as discussed above.

Figure 3:
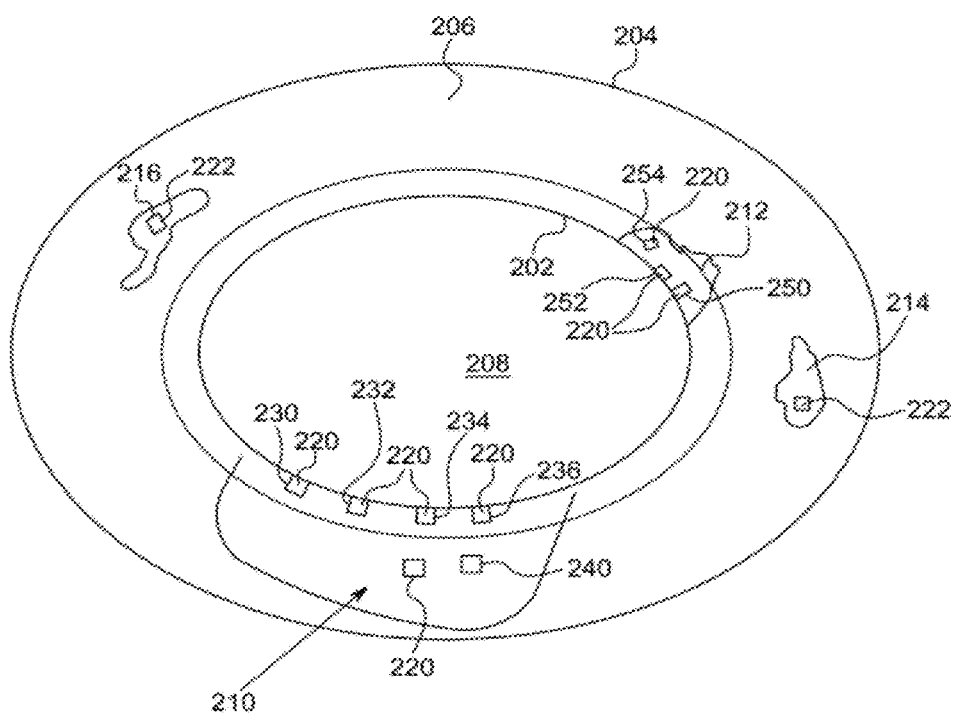
FIG. 3 is a simplified illustration of an exemplary myocardium image formed in accordance with various embodiments.

In operation, the clustering analysis is performed on the clusters described above to determine the location of each of the voxels in the clusters. More specifically, the cluster analysis then determines the location of the voxels classified as non-viable voxels. For example, FIG. 3 is a simplified illustration of a portion of an exemplary heart 200 that includes a endocardium 202, a epicardium 204, and a myocardium 206 defined therebetween. In the exemplary embodiment, the FIG. 3 illustrates the myocardium 206 of the left ventricle 208. As shown in FIG. 3, the voxels are initially clustered based on the Z-score and/or the T-score to generate a plurality of clusters 210, 212, 214, and 216. It should be realized that although only four clusters are shown, that method 100 generates many clusters that may include viable voxels, non-viable voxels, or a combination thereof.

More specifically, physiologically, a perfusion defect is a result of the inability of some blood vessels to provide enough blood to tissue cells. In the myocardium, the first tissue cells impacted are typically the tissue cells that are located the furthest from the coronary vessels on the myocardium surface. Thus, an ischemia, i.e. a perfusion defect, typically starts in the myocardium from the endocardium layer in contact with the left ventricle. Therefore, to identify the non-viable voxels the cluster analysis is then applied to voxels included in the non-viable clusters, e.g., the hypo-dense voxels using a seed algorithm, for example, as discussed in more detail below. Specifically, if any of the voxels identified as non-viable based on the Z-score or T-score, are non-connected (see explanation above) to the endocardium 202, the voxels are removed from the cluster including non-viable voxels to a cluster of viable voxels.

In the exemplary embodiment, to determine the location of each of the voxels, the non-viable voxels are filtered using, for example, the seed algorithm. More specifically, and referring again to FIG. 3, there is shown two clusters 210 and 212 that include non-viable voxels 220 and 222 and two clusters 214 and 216 that include non-viable voxels 222 as determined based on the voxel density values discussed above. Accordingly, a first voxel 230 is selected as a seed voxel. It should be realized that only voxels connected to the endocardium may be selected as a seed. For example, if the first voxel 230 is connected to the endocardium 202, the first voxel 230 is classified as a non-viable voxel and remains in the cluster 210. Accordingly, each cluster with at least one voxel connected to the endocardium 202 is classified as a non-viable voxel and remains in the cluster of non-viable voxels. For example, voxels 230, 232, 234, and 236 are connected to the endocardium 202 and therefore the cluster 210 remains a non-viable cluster. Additionally, voxels 250 and 252 are connected to the endocardium 202, and therefore the cluster 212 remains a non-viable cluster. However, clusters 214 and 216 have no voxels connected to the endocardium, therefore they are removed from non-viable clusters and added into viable clusters. Accordingly, at 110, the voxels are partitioned into clusters wherein a first set of clusters, e.g. clusters 210 and 212, include non-viable voxels that are connected to the endocardium 202 and a second set of clusters, e.g. clusters 214 and 216, include viable voxels.

Figure 4:
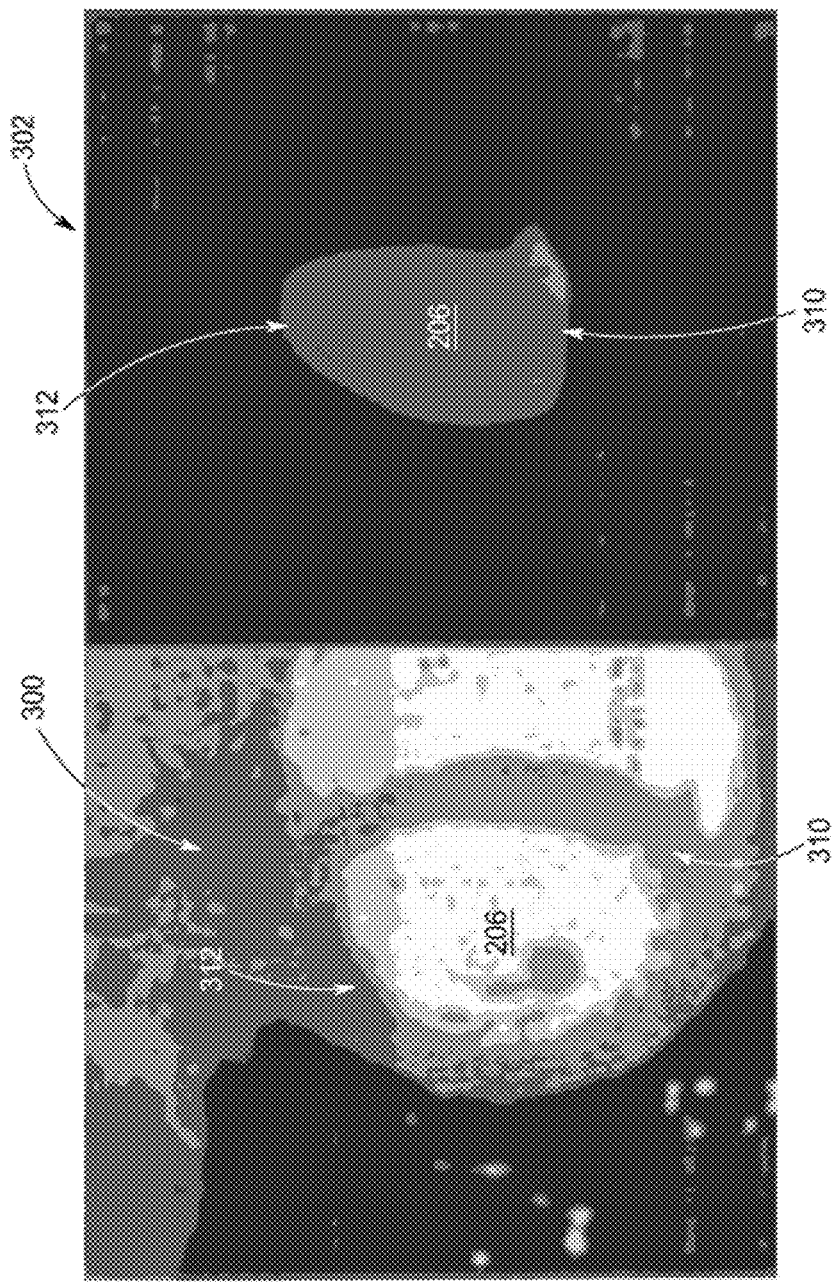
FIG. 4 is an exemplary two-dimensional (2D) CT image formed in accordance with various embodiments.

FIG. 4 illustrates two exemplary 2D CT images 300 and 302 that may be generated using the clusters 210, 212, 214, and 216. More specifically, image 300 is a 2D CT image and image 302 is a 3D CT image of the myocardium 206 wherein a first area 310 represents the viable clusters 214 and 216 and the second area 312 represents the non-viable clusters 210 and 212.

At 112, the clusters 210, 212, 214, and 216 and/or the images 300 and 302, are utilized to generate at least one pseudo-nuclear map of the myocardium 206. A pseudo-nuclear map is defined herein as a map that is utilized to convert colors, shading, and/or indicia utilized to generate a CT image to colors, shading, and/or indicia that is similar to a conventional PET image. In the exemplary embodiment, to generate the pseudo-nuclear map at 112, the Hounsfield units for each voxel in the CT images 300 and 302 are converted into values that represent the magnitude of a coincidence event that would be observed in a conventional PET imaging system. The Hounsfield units may be converted to pseudo-PET values using a conversion scale, a conversion map, or other suitable techniques.

Figure 5:
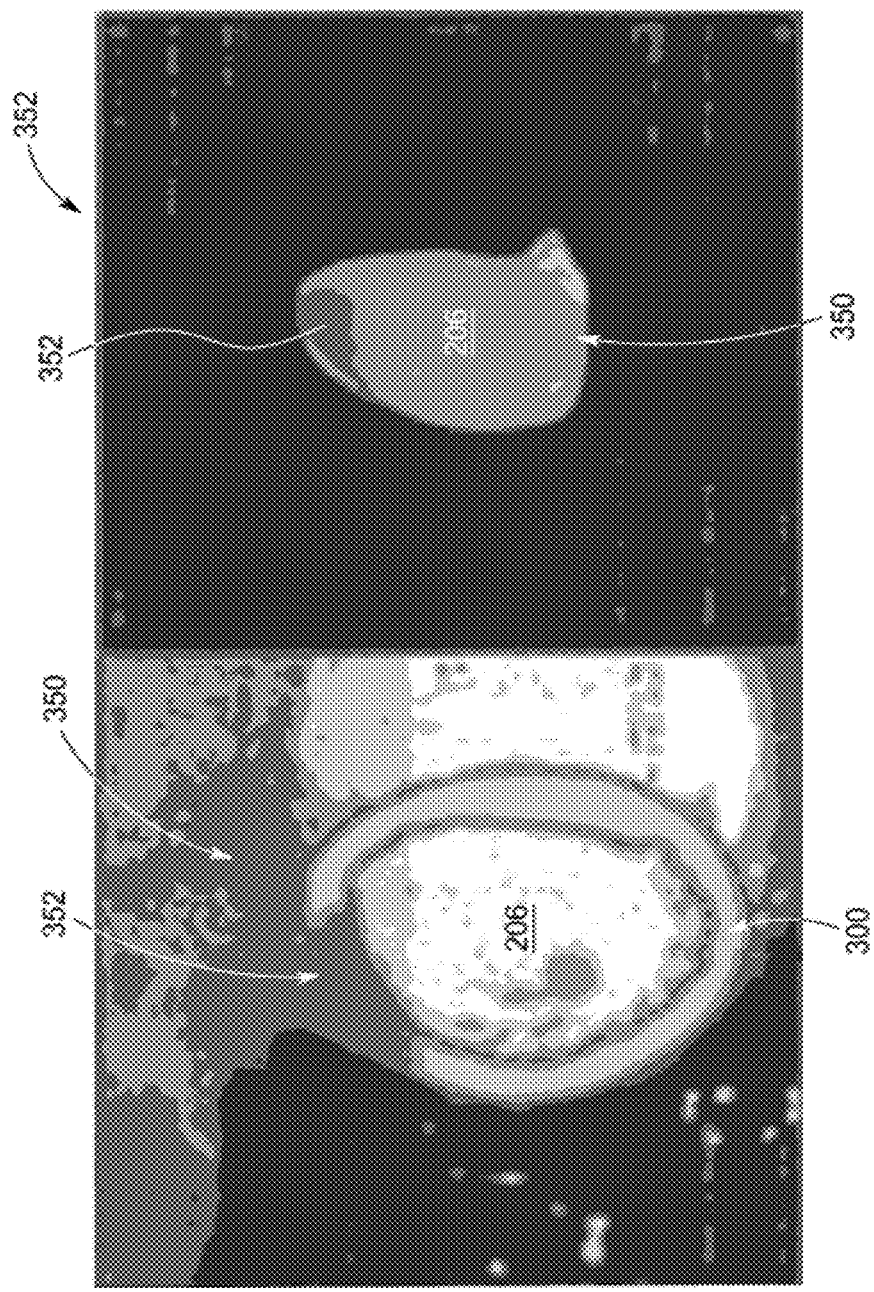
FIG. 5 is an exemplary 2D pseudo-nuclear image formed in accordance with various embodiments.

At 114, the pseudo-nuclear maps are utilized to generate the 2D pseudo-PET images 350 and 352 shown in FIG. 5. For example, FIG. 5 illustrates two exemplary 2D images 350 and 352 that may be generated using the pseudo-nuclear map described above. More specifically, images 350 and 352 are 2D pseudo-Positron Emission Tomography (PET) images of the myocardium 206 wherein a first area 360 represents the viable clusters 210 and 212 and the second area 352 represents the non-viable clusters 214 and 216. In operation, the pseudo-PET images 350 and 352 facilitate displaying perfusion viability with a rendered volume that is similar to the rendered volume obtained using a conventional PET imaging system. Accordingly, the images 350 and 352 may be easily compared with conventional nuclear images of the same subject to enable physicians and radiologists to perform diagnosis. The images 350 and 352 are generated using CT projection data, therefore the images 350 and 352 may be generated faster than conventional PET images while exposing the subject 24 to a reduced quantity of radiation because of the reduced scan time used to generate the projection data. Additionally, other filtering or processing may be performed, for example, such that a partial volume effect may be recreated by convoluting a 3D Gaussian filter with the images 350 and 352.

Figure 6:
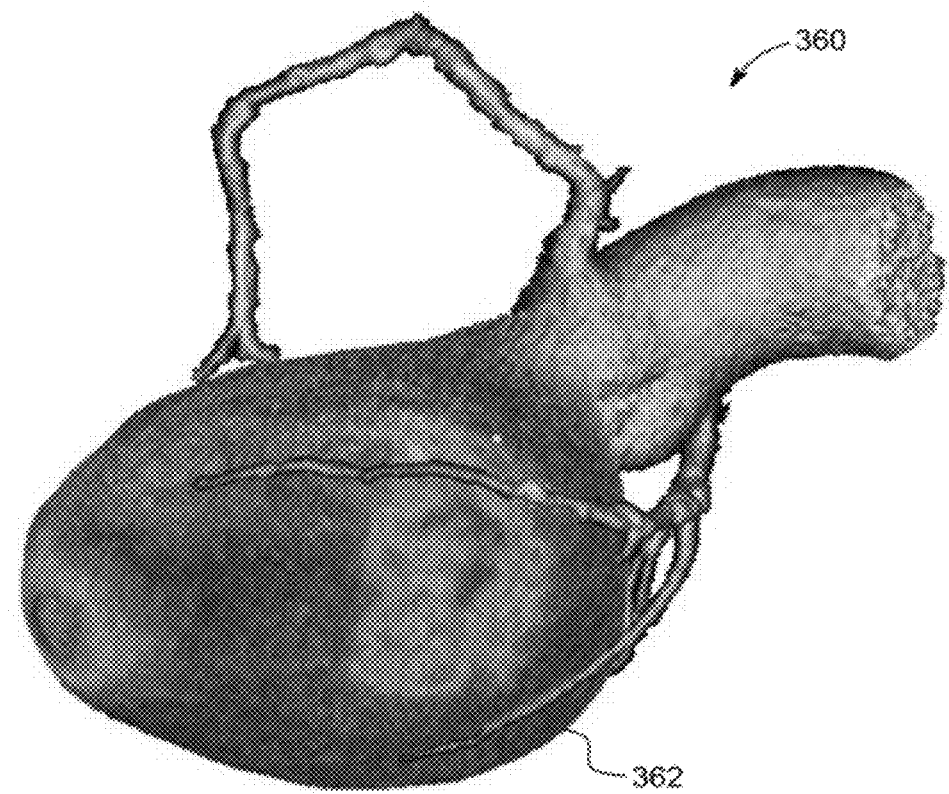
FIG. 6 is an exemplary three-dimensional (3D) pseudo-nuclear image formed in accordance with various embodiments.

At 116, the pseudo-nuclear maps may also be utilized to generate at least one 3D pseudo-PET image such as the 3D pseudo-PET image 360 shown in FIG. 6. The image 360 may be generated by applying a suitable volume rendering (VR) technique to the pseudo-nuclear maps such that the displayed values correspond to the mean values of volume intensities along a ray. As shown in FIG. 6, the image 360 illustrates a heart 362 and a coronary tree 364. In the exemplary embodiment, the coronary tree 364 is generated using a segmentation algorithm. Initially, the structure corresponding to the coronaries is defined. The segmentation algorithm then segments the coronary trees to define a volume that represents the coronary tree. The segmentation algorithm may be implemented using a threshold technique. For example, the range of density values that correspond to the coronary tree are defined. The segmentation algorithm then segments the volume to generate a volume that includes only the coronary tree. The segmented volume is then utilized to generate the image 360 of the coronary tree. The image of the coronary tree may be displayed concurrently with the perfusion image of the myocardium described above.

Figure 7:
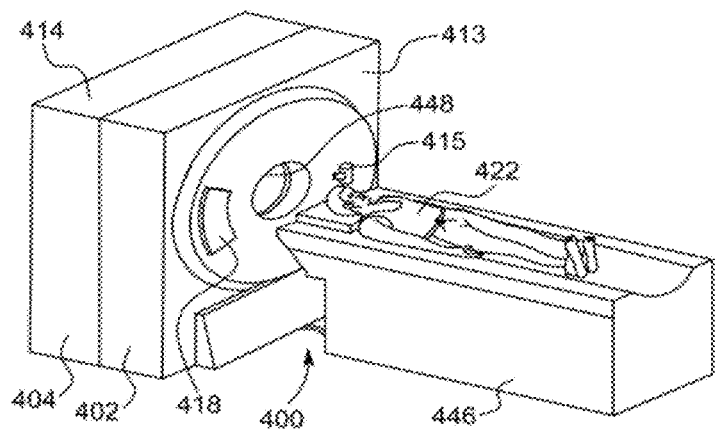
FIG. 7 is a perspective view of an exemplary imaging system formed in accordance with various embodiments.
Figure 8:
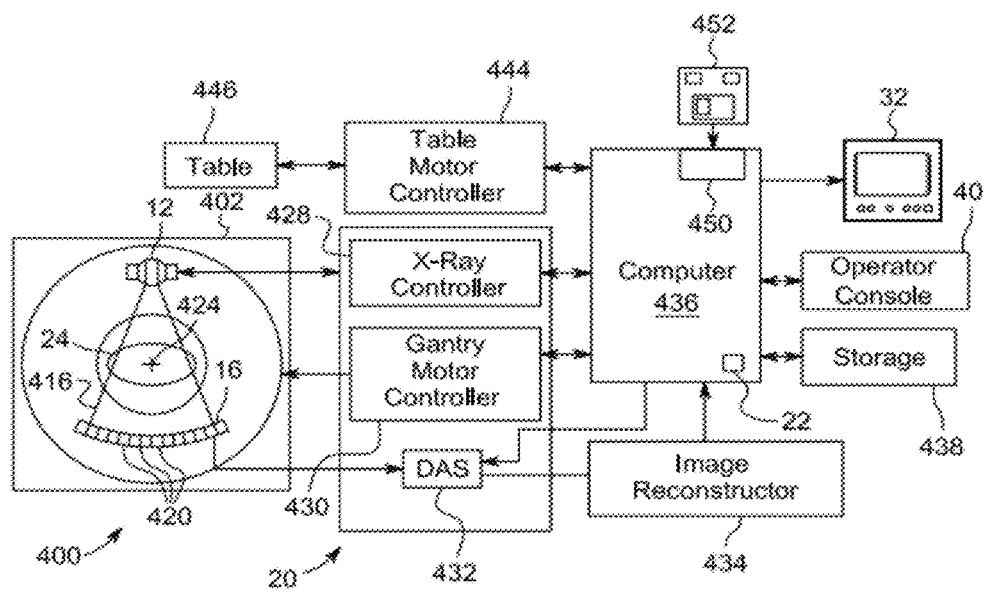
FIG. 8 is a schematic block diagram of the imaging system shown in FIG. 7.

FIG. 7 is a perspective view of an exemplary imaging system 400 that may be configured to implement the various methods described herein. FIG. 8 is a schematic block diagram of the imaging system 400 (shown in FIG. 7). In the exemplary embodiment, the imaging system 400 is a multi-modal imaging system and includes a first modality unit 402 and a second modality unit 404. The modality units 402 and 404 enable system 400 to scan an object, for example, the subject 24, in a first modality using the first modality unit 402 and to scan the subject 24 in a second modality using the second modality unit 404. System 400 allows for multiple scans in different modalities to facilitate an increased diagnostic capability over single modality systems.

In one embodiment, the multi-modal imaging system 400 is a Computed Tomography/Positron Emission Tomography (CT/PET) imaging system 400. CT/PET system 400 includes a first gantry 413 associated with the first modality unit 402 and a second gantry 414 associated with the second modality unit 404. In other embodiments, modalities other than CT and PET may be employed with imaging system 400. The gantry 413 includes the first modality unit 402 that has the x-ray source 12 that projects a beam of x-rays 416 toward a detector array 16 on the opposite side of the gantry 413. The detector array 16 is formed by a plurality of detector rows (not shown) including a plurality of detector elements 420 that together sense the projected x-rays that pass through an object, such as the subject 24. Each detector element 420 produces an electrical signal that represents the intensity of an impinging x-ray beam and therefore, allows estimation of the attenuation of the beam as it passes through the subject 24.

During a scan, to acquire x-ray projection data, the gantry 413 and the components mounted thereon rotate about an examination axis 424. FIG. 8 shows only a single row of detector elements 420 (i.e., a detector row). However, the detector array 16 may be configured as a multislice detector array having a plurality of parallel detector rows of detector elements 420 such that projection data corresponding to a plurality of slices can be acquired simultaneously during a scan.

The rotation of the gantry 413, and the operation of x-ray source 12, are controlled by the system controller 20 of the CT/PET system 400. The system controller 20 includes an x-ray controller 428 that provides power and timing signals to the x-ray source 12 and a gantry motor controller 430 that controls the rotational speed and position of the gantry 413. A data acquisition system (DAS) 432 of the system controller 20 samples data from detector elements 20 for subsequent processing as described above. An image reconstructor 434 receives sampled and digitized x-ray projection data from the DAS 432 and performs high-speed image reconstruction. The reconstructed image is transmitted as an input to a computer 436 which stores the image in a storage device 438. The computer 436 may be programmed to implement various embodiments described herein. More specifically, the computer 436 may include the image processing module 22 that is programmed to carry out the various methods described herein.

The computer 436 also receives commands and scanning parameters from an operator via the operator workstation 40 that has an input device, such as, keyboard. The associated display 32 allows the operator to observe the reconstructed image and other data from the computer 436. The operator supplied commands and parameters are used by computer 436 to provide control signals and information to the DAS 432, the system controller 20, and the gantry motor controller 430. In addition, the computer 436 operates a table motor controller 444 which controls a motorized table 446 to position the subject 24 in the gantry 413 and 414. Specifically, the table 446 moves portions of the subject 24 through a gantry opening 448.

In one embodiment, the computer 436 includes a read/write device 450, for example, a floppy disk drive, CD-ROM drive, DVD drive, magnetic optical disk (MOD) device, or any other digital device including a network connecting device such as an Ethernet device for reading instructions and/or data from a non-transitory computer-readable medium 452, such as a floppy disk, a CD-ROM, a DVD or an other digital source such as a network or the Internet, as well as yet to be developed digital means. In another embodiment, the computer 436 executes instructions stored in firmware (not shown). The computer 436 is programmed to perform functions as described herein, and as used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein. CT/PET system 400 also includes a plurality of PET detectors (not shown) including a plurality of detector elements.

A technical effect of the various embodiments described herein is to provide a clustering result that improves images. The improved images may display perfusion viability in a format that is similar to those obtained with nuclear medicine. The resulting images may be easily compared with nuclear images to enable a physician to perform a diagnosis of the subject. More specifically, the clustering results in a new data volume that is computed with intensities corresponding to typical values for nuclear medicine images, with or without a perfusion defect.

Various embodiments described herein provide a tangible and non-transitory machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method for displaying image data for a myocardium of a heart, said method comprising:
acquiring a three-dimensional (3D) projection dataset using a Computed Tomography (CT) imaging system;
performing a segmentation of the 3D projection dataset to identify a plurality of voxels representing heart cavity voxels;
performing a segmentation of the heart cavity voxels to identify a plurality of voxels representing myocardium voxels;
grouping the myocardium voxels into viable clusters and potential non-viable clusters based on a density of the myocardium voxels;
re-grouping each of the potential non-viable clusters into the viable clusters or non-viable clusters based on locations of the myocardium voxels included in the potential non-viable clusters with respect to the endocardium; and
generating a 3D image of the myocardium using the viable clusters and the non-viable clusters.

2. The method of claim 1, wherein the re-grouping operation further comprises selecting a seed voxel from one of the potential non-viable clusters based on a location of the seed voxel, wherein the location of the seed voxel is connected to the endocardium and classified as a non-viable voxel.

3. The method of claim 1,
wherein the segmentation of the heart cavity voxels further comprises extracting contours of the myocardium from the heart cavity voxels.

4. The method of claim 1, further comprising:
generating a pseudo-nuclear map using the viable and non-viable clusters; and
generating a two-dimensional (2D) pseudo-nuclear image of the myocardium using the pseudo-nuclear map.

5. The method of claim 1, further comprising:
generating a pseudo-nuclear map using the viable and non-viable clusters;
performing a segmentation algorithm on the 3D projection data to define a volume that represents a coronary tree; and
generating a three-dimensional (3D) pseudo-nuclear image of a heart using the pseudo nuclear map and the coronary tree.

6. The method of claim 4, wherein generating a pseudo-nuclear map comprises converting a voxel Hounsfield number to an pseudo-equivalent PET value.

7. The method of claim 1, wherein the grouping further comprises classifying the myocardium voxels into the viable clusters and potential non-viable clusters-based on a Z-score or T-score, and determining locations of the myocardium voxels within the potential non-viable clusters using a seed algorithm.

8. A Computed Tomography (CT) imaging system comprising:
an x-ray source;
a detector configured to receive x-rays from the x-ray source; and
a computer coupled to the detector, the computer being programmed to:
acquire a three-dimensional (3D) projection dataset using a Computed Tomography (CT) imaging system;
perform a segmentation of the 3D projection dataset to identify a plurality of voxels representing heart cavity voxels;
perform a segmentation of the heart cavity voxels to identify a plurality of voxels representing myocardium voxels;
group the myocardium voxels into viable clusters and potential non-viable clusters based on a density of the myocardium voxels;
re-grouping each of the potential non-viable clusters into the viable clusters or non-viable clusters based on locations of the myocardium voxels included in the potential non-viable clusters with respect to the endocardium; and
generate a 3D image of the myocardium using the viable clusters and the non-viable clusters.

9. The CT imaging system of claim 8, wherein the computer for the re-grouping operation is further programmed to select a seed voxel from the potential non-viable cluster based on a location of the seed voxel, wherein the location of the seed voxel is connected to the endocardium and classified as a non-viable voxel.

10. The CT imaging system of claim 8, wherein the computer is further programmed to
extract contours of the myocardium from the heart cavity voxels.

11. The CT imaging system of claim 8, wherein the computer is further programmed to:
generate a pseudo-nuclear map using the viable and non-viable clusters; and
generate a two-dimensional (2D) pseudo-nuclear image of the myocardium using the pseudo-nuclear map.

12. The CT imaging system of claim 8, wherein the computer is further programmed to:
generate a pseudo-nuclear map using the viable and non-viable clusters;
performing a segmentation algorithm on the 3D projection data to define a volume that represents a coronary tree; and
generate a three-dimensional (3D) pseudo-nuclear image of a heart and the coronary tree using the pseudo-nuclear map.

13. The CT imaging system of claim 8, wherein the computer is further programmed to convert a voxel Hounsfield number to an equivalent PET value.

14. The CT imaging system of claim 8, wherein the computer is further programmed to classify the myocardium voxels into the viable and non-viable clusters based on a Z-score or T-score, and determine locations of myocardium voxels within the potential non-viable clusters using a seed algorithm.

15. A non-transitory computer readable medium encoded with a program to instruct a computer to:
acquire a three-dimensional (3D) projection dataset using a Computed Tomography (CT) imaging system;
perform a segmentation of the 3D projection dataset to identify a plurality of voxels representing heart cavity voxels;
perform a segmentation of the heart cavity voxels to identify a plurality of voxels representing myocardium voxels;
group the myocardium voxels into viable clusters and potential non-viable clusters based on a density of the myocardium voxels;

re-grouping each of the potential non-viable clusters into the viable clusters or non-viable clusters based on locations of the myocardium voxels included in the potential non-viable clusters with respect to the endocardium; and generate a 3D image of the myocardium using the viable clusters and the non-viable clusters.

16. A computer readable medium in accordance with claim 15, wherein the program is programmed to extract contours of the myocardium from the heart cavity voxels.

17. A computer readable medium in accordance with claim 15 wherein the program is programmed to further instruct a computer to:

generate a pseudo-nuclear map using the viable and non-viable clusters; and generate a two-dimensional (2D) pseudo-nuclear image of the myocardium using the pseudo-nuclear map.

18. A computer readable medium in accordance with claim 15 wherein the program is programmed to further instruct a computer to:

generate a pseudo-nuclear map using the viable and non-viable clusters;

perform a segmentation algorithm on the 3D projection data to define a volume that represents a coronary tree; and generate a three-dimensional (3D) pseudo-nuclear image of a heart using the pseudo nuclear map and the coronary tree.

* * * * *